(12) United States Patent
Zimmermann et al.

(10) Patent No.: US 7,083,761 B2
(45) Date of Patent: Aug. 1, 2006

(54) CONTAINER AND APPARATUS FOR TISSUE PROCESSING FOR TISSUE EMBEDDING

(75) Inventors: Michael Zimmermann, Leopoldsdorf (AT); Anton Lang, Vienna (AT); Heinz Plank, Neudorf (AT); Rainer Wogritsch, Vienna (AT)

(73) Assignee: Leica Mikrosysteme GmbH, Vienna (AT)

( * ) Notice: Subject to any disclaimer, the term of this patent is extended or adjusted under 35 U.S.C. 154(b) by 535 days.

(21) Appl. No.: 10/153,949

(22) Filed: May 23, 2002

(65) Prior Publication Data
US 2002/0193814 A1   Dec. 19, 2002

(30) Foreign Application Priority Data
May 25, 2001   (EP)   .................... 01112663

(51) Int. Cl.
*B01L 3/00* (2006.01)

(52) U.S. Cl. ..................... 422/99; 435/288.5

(58) Field of Classification Search .............. 422/99; 435/288.5
See application file for complete search history.

(56) References Cited

U.S. PATENT DOCUMENTS

| | | | | |
|---|---|---|---|---|
| 4,688,517 A | | 8/1987 | Hollman | 118/421 |
| 5,080,869 A | * | 1/1992 | McCormick | 422/102 |
| 5,255,816 A | * | 10/1993 | Trepp | 220/529 |
| 5,624,418 A | * | 4/1997 | Shepard | 604/319 |
| 6,309,607 B1 | * | 10/2001 | Johnston et al. | 422/104 |

* cited by examiner

Primary Examiner—Jill Warden
Assistant Examiner—Natalia Levkovich
(74) Attorney, Agent, or Firm—Simpson & Simpson, PLLC

(57) ABSTRACT

A container (2) for tissue preparation for the tissue embedding, having a base body (4), that is formed out cylindrical shaped side wall (5), a floor (6) and several bridges (50). The bridges (50) subdivide the container (2) in several sub-containers (52). The side wall (5) has a plurality of slit shaped openings (12), that extend essentially over the total height of the side wall (5).

3 Claims, 5 Drawing Sheets

CONTAINER AND APPARATUS FOR TISSUE PROCESSING FOR TISSUE EMBEDDING

RELATED APPLICATION

This patent application claims the benefit of the priority of European patent application number 01 112 663.8, filed on May 25, 2001, which is incorporated by reference herein.

FIELD OF THE INVENTION

The invention refers to a container for tissue processing for tissue embedding and an apparatus for tissue processing for tissue embedding.

In particular the invention refers to a container for tissue processing for the tissue embedding, having a base body, that is formed out of cylindrical shaped side wall, a floor and several bridges, whereby the bridges subdivide the container into several sub-containers.

In addition the invention refers to an apparatus for tissue preparation for the tissue embedding having a transport plate onto which a plurality of processing containers are attached.

BACKGROUND OF THE INVENTION

The U.S. Pat. No. 4,688,517 discloses an apparatus for processing tissue samples. On a rotatable table a plurality of processing containers are provided for the sample processing. The table is rotatable, so that the processing containers can be transported to a processing station, at which the tissue samples are successively immersed in different processing liquids. For a suitable tempering of the actually used processing liquids a heating and cooling device is permanently mounted to the housing of the apparatus. The table is not only rotatable but also raisable and lowerable in the direction of the axle. The processing containers are only snapped into recesses of the transport table. A firm and defined placement of the processing containers on the table is not provided.

For tissue processing for the tissue embedding the RMC™ and the LYNX™ tissue processor uses containers that have a cylindrical side wall and do not have openings for the entering or exiting of processing liquid. Next to the side wall there is a conical part that is getting narrower and narrower compared to the part with the cylindrical side wall. The conical part of the side wall is provided with corresponding elongated openings that make the entering and exiting of the processing liquids possible. If the containers are stacked, then each container is to be provided with a cover in order to ensure that no parts of the tissue are washed out of the container during the process. The use of a plurality of parts when preparing the samples for the process does not make the handling easy. In addition there is the danger that the tissue samples are washed out of the container if no covers are used for example.

SUMMARY OF THE INVENTION

It is the object of the invention to provide a container designed for tissue processing for tissue embedding. The container is to facilitate the handling of the process and at the same time to ensure that tissue samples are well surrounded by the process liquids in the processing container. In addition the container is to minimize the amount of the processing liquid that is carried over from one container to the next.

The objective is solved by a container for tissue preparation for the tissue embedding, which comprises: a base body that has a cylindrical shaped side wall, a floor and several bridges, whereby the bridges subdivide the containers into several sub-containers and a plurality of slit shaped openings are formed in the cylindrical shaped side wall and extend essentially over the total height of the cylindrical shaped side wall.

It is the objective of the invention to provide an apparatus for tissue processing for tissue embedding that makes a reliable tissue preparation for tissue embedding possible whilst the amount of the different processing liquids that are carried over from one processing container to the next is minimized.

The above objective is solved by an apparatus which comprises:
  a transport plate,
  a plurality of processing containers are attachable on the transport plate,
  a rod wherein at least one container for tissue preparation for the tissue embedding is on the rod, which is provided with a holding element, and
  an arm onto which the holding element is hangable wherein the arm moves the containers up and down in the processing containers.

The advantage of the invention is that due to the design of the containers in a cylindrical form that extends over their whole height, it is possible to put a plurality of containers together in a stack, whereby the floor of one container provides the cover for the container arranged downstream on the stack. When stacking containers this is especially advantageous since the number of parts to be handled is to be kept to a minimum. In addition it can be excluded that tissue samples are washed out of the container during the process simply because no cover has been used when stacking the containers.

In addition the base container has a plurality of slit shaped openings that extend over the whole height of the side wall. The openings are meant to ensure the exchange of the process liquid and thereby to minimize the amount of process liquid that is carried over from the apparatus of one processing container to the tissue processing for tissue embedding.

Furthermore, the container has a base body wherein a plurality of bridges are arranged equally and the bridges end on one side at the side wall of the base body and on the other side at a central hollow cylinder that is used for stacking the base containers. The base containers are fixed to a rod with the help of a securing element. The rod is led through the central hollow cylinder and thereby defining an exact position of the base bodies within the stack.

When using only one base container the container is closed with a cover with the base body and the cover having a groove formed. The groove in the cover and the groove in the base body are in line in case the cover is on the base body and arranged accordingly.

The apparatus for tissue preparation for the tissue embedding bears an additional advantage. The apparatus has a transport plate onto which a plurality of processing containers is attached. At least one container for tissue preparation for the tissue embedding is positioned on a rod, which is provided with a holding element. The holding element is hangable onto an arm of the apparatus. With the help of the appropriate mechanics the arm can be moved in such a way that the container with the tissue sample can be moved up and down in the processing liquid in the processing containers in order to ensure that the processing liquid is well washed round the tissue sample.

BRIEF DESCRIPTION OF THE DRAWINGS

In the drawing the invention is schematically shown and described on the basis of the figures below. The figures show in.

DETAILED DESCRIPTION OF THE PREFERRED EMBODIMENT

Figure 1:
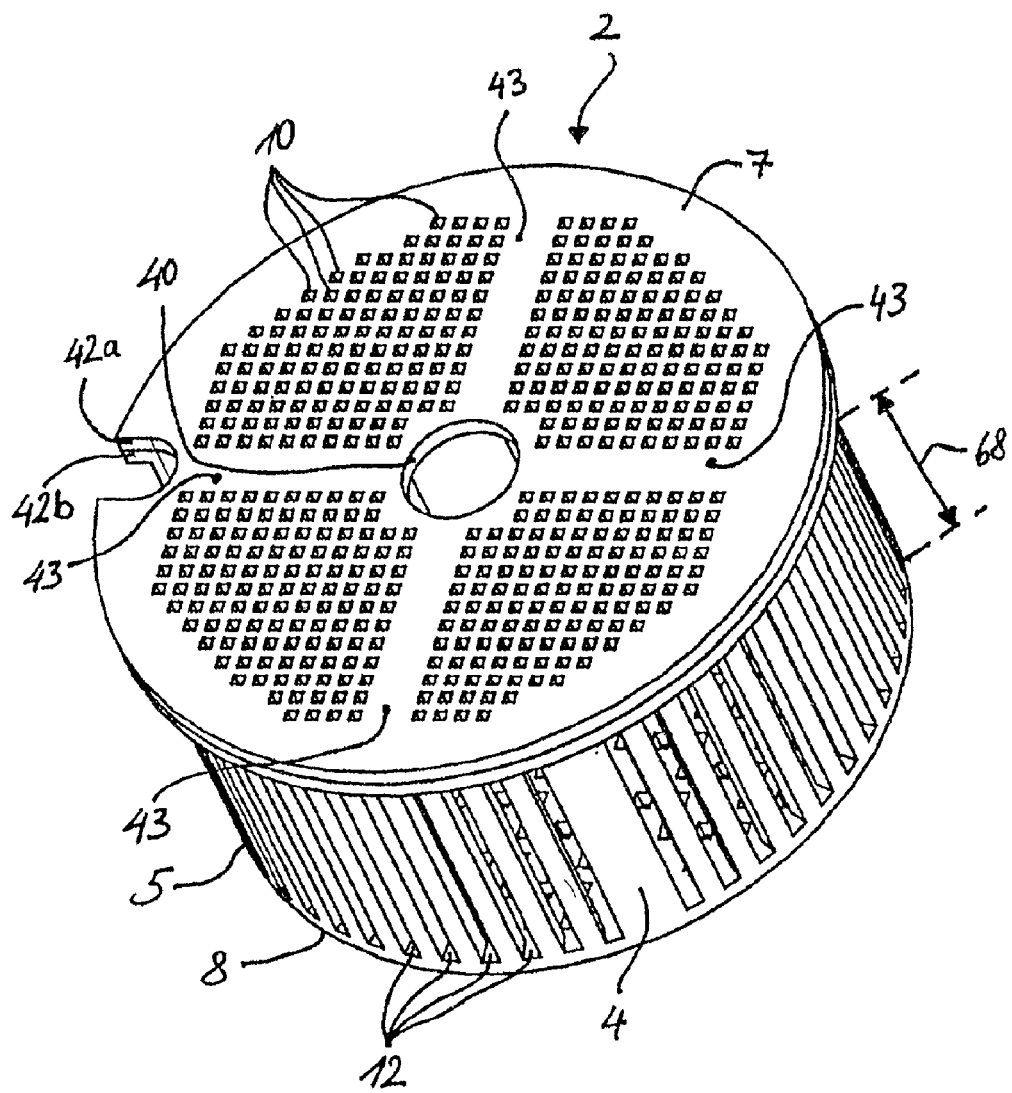
FIG. 1 is a perspective view of the processing container for tissue preparation for tissue embedding.

FIG. 1 shows a processing container 2 for tissue preparation for tissue embedding in a perspective view. The processing container 2 has a cylindrical base body 4 with a side wall 5 and a floor 6 and is open to the top. A removable cover 7 can be attached to the base body 4. Both the cover 7 and the floor 6 have a plurality of openings 10 that support the entering and exiting of the processing liquid. The side wall 5 of the base body 4 has a plurality of slit shaped openings 12 in the direction of the axle of the processing container 2. The slit shaped openings 12 extend over the whole height 68 of the cylindrical side wall 5. The slit shaped openings 12 in the side wall 5 are also responsible for a steady, fast and total exchange of the processing liquid. The cover 7 has a central circular opening 40. As shown in FIG. 3 a rod is led through the opening to stack a plurality of containers 2. On the edge of the cover 7 there is a groove that is shaped as an elongated groove 42b in the direction of the axle in the side wall 5 of the base body 4. Furthermore, there are several bridges in the cover 43 that are meant to support the stability of the shape of the cover 7. Furthermore, the number of the bridges in the cover 43 depends on the number of bridges in the base element 50 that subdivide the space surrounded by side wall 5 of the base body 4 in several sub-containers 52 (see FIG. 2a).

Figure 2B:
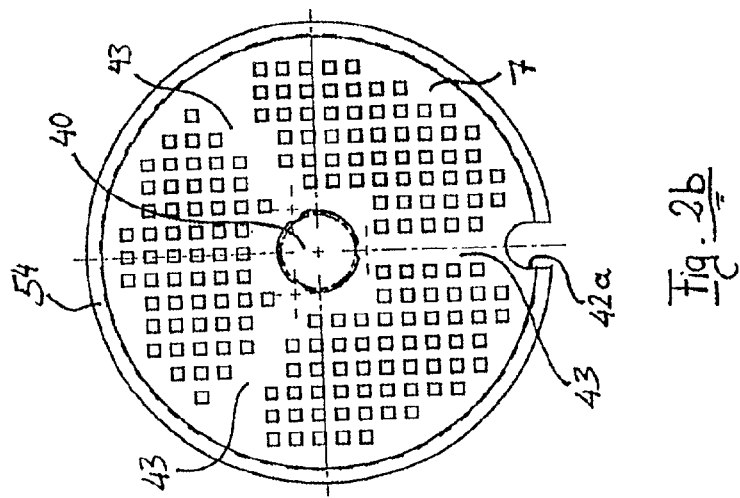
FIG. 2b is a top view on the cover for the container for tissue preparation.
Figure 2C:
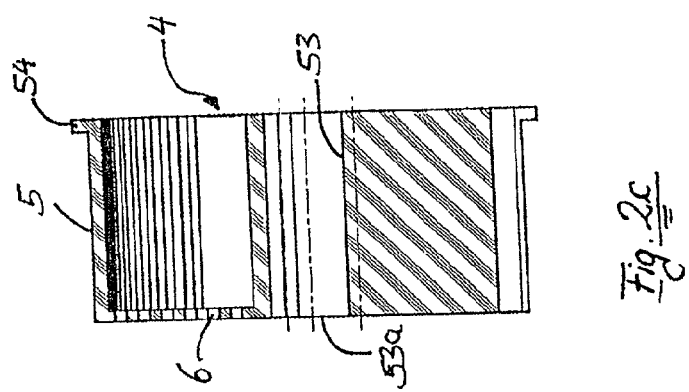
FIG. 2c is a side view of the container for tissue preparation for tissue embedding.
Figure 2A:
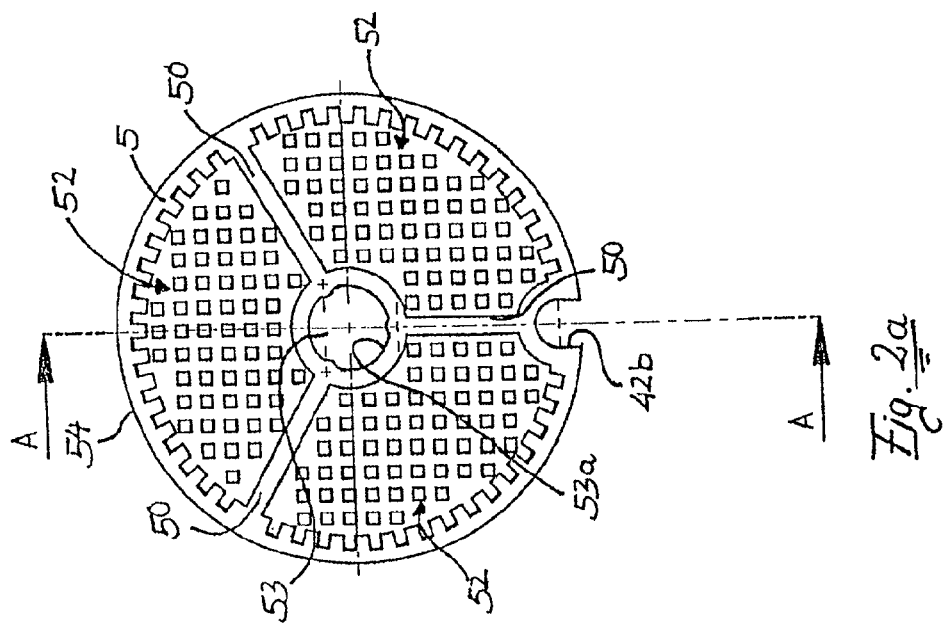
FIG. 2a is a top view on the processing container for tissue preparation for tissue embedding uncovered.
Figure 3:
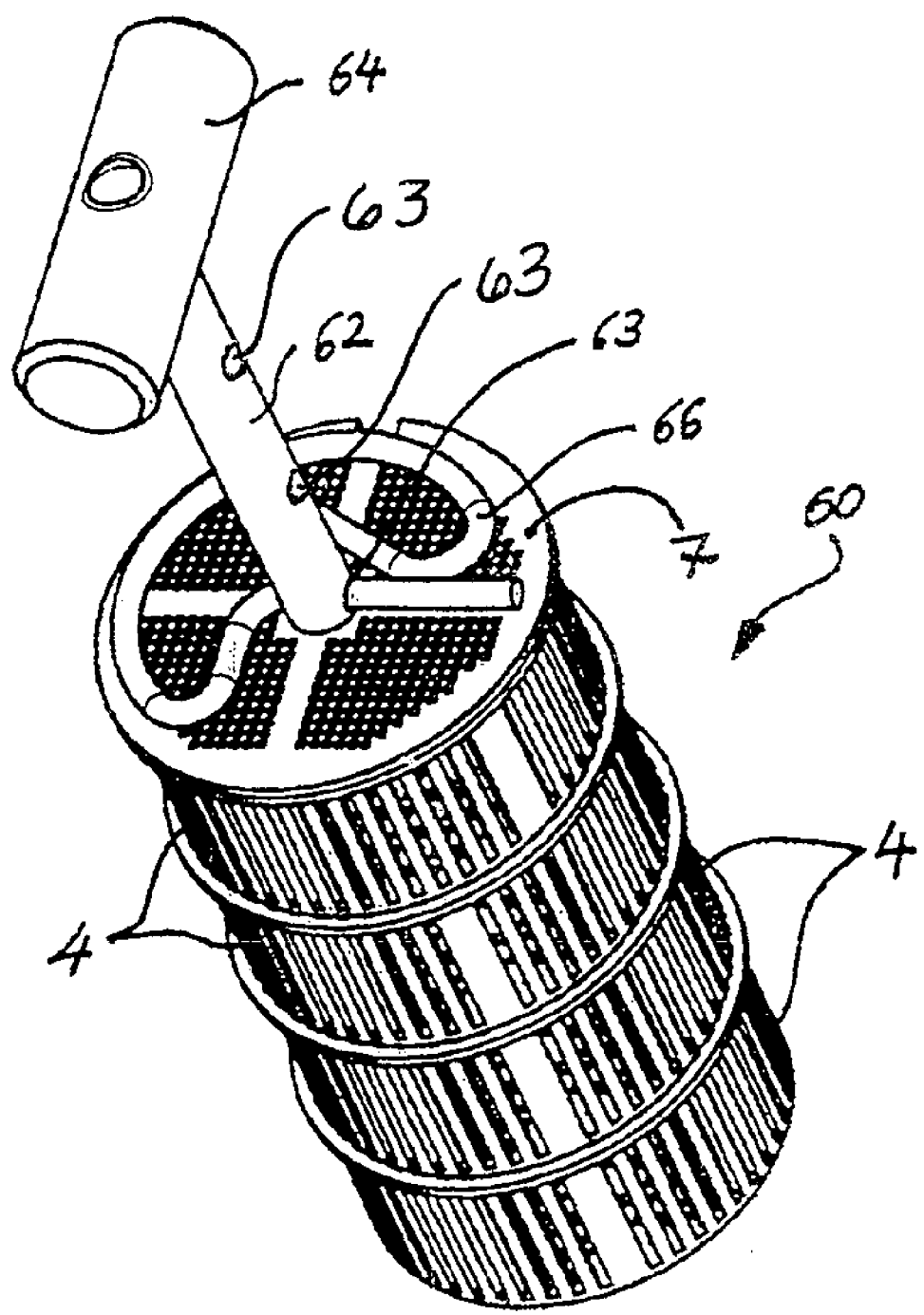
FIG. 3 is a perspective view of containers for tissue preparation for tissue embedding, wherein the containers are put together in a stack.

FIG. 2a shows an example of how the cylindrical base body 4 is subdivided in three, preferable, similar sub-containers 52. One of the bridges in the base element 50 ends at the elongated groove 42 located at the side wall 5 of the cylindrical base body 4. The tissue samples stored in the sub-containers 52 are thereby clearly classified and documented. The bridges in the base element 50 end on one side at the side wall 5 and on the other side at a central hollow cylinder 53. The hollow cylinder has a central opening 53a. The base body 4 has a circumferential edge 54 that has a diameter slightly larger than the cylindrical side wall 5.

FIG. 2b shows the cover 7 of the base body 4. On cover 7 the bridge in the cover 43 is arranged in such a way that it is in line with bridges in the base element 50 in the base body 4. Cover 7 is put on the base body 4 in such a way that the groove 42a in cover 7 is in line with the elongated groove 42b in the base body 4. This means that the bridges in the cover 43 are located exactly above the bridges in the base element 50. This prevents the tissue samples located in the sub-containers 52 to be washed out of the sub-containers 52 by the processing liquids during the preparation process. Cover 7 shows a plurality of openings 10 like those located on the floor 6 of the base body 4 to ensure the flow of the processing liquid and to minimize the amount of processing liquid being carried over. The circular opening 40 in cover 7 is in line with the central opening 53a when the removable cover 7 is put on the base body 4.

FIG. 2c shows a cross section of the base body 4. The hollow cylinder 53 extends in the direction of the axle over the base body 4 and the central opening 53a makes it possible to reach through the base body 4. The floor 6 of the base body 4 is also flat. The side wall 5 has a circumferential edge 54, which, as mentioned above, has a larger diameter than the base body 4.

FIG. 3 shows a possibility of how several base bodies 4 are put together in a stack 60. This stack 60 can then be fed to an apparatus 1 (see figures 4 and 5) for preparation of the processing liquids. The example described here shows four base bodies 4 that make up one stack 60. The number of the base bodies 4 that make up a unit of 60 is simply one choice out of several possibilities. Other combinations are possible. The base bodies 4 are stacked one above the other in such a way that the floor 6 of the base body 4 is the cover for the base body 4 arranged downstream on the stack 60. The base body 4 on top of stack 60 is covered with a cover 7. The base body 4 and the cover 7 are adjusted with the help of a rod 62 that is led through the hollow cylinder of each base body 4 or through the opening 40 in the cover 7. The rod is equipped with several drillings 63, which serve to adjust the securing element 66. The drillings 63 are located along the rod 62 in such a way that at any time any number of base bodies 4 can be put together to a stack 60. The side of rod 62 not facing the base bodies 4 is equipped with a holding element 66 that serves to attach the stack 60 to the apparatus 1.

Figure 4:
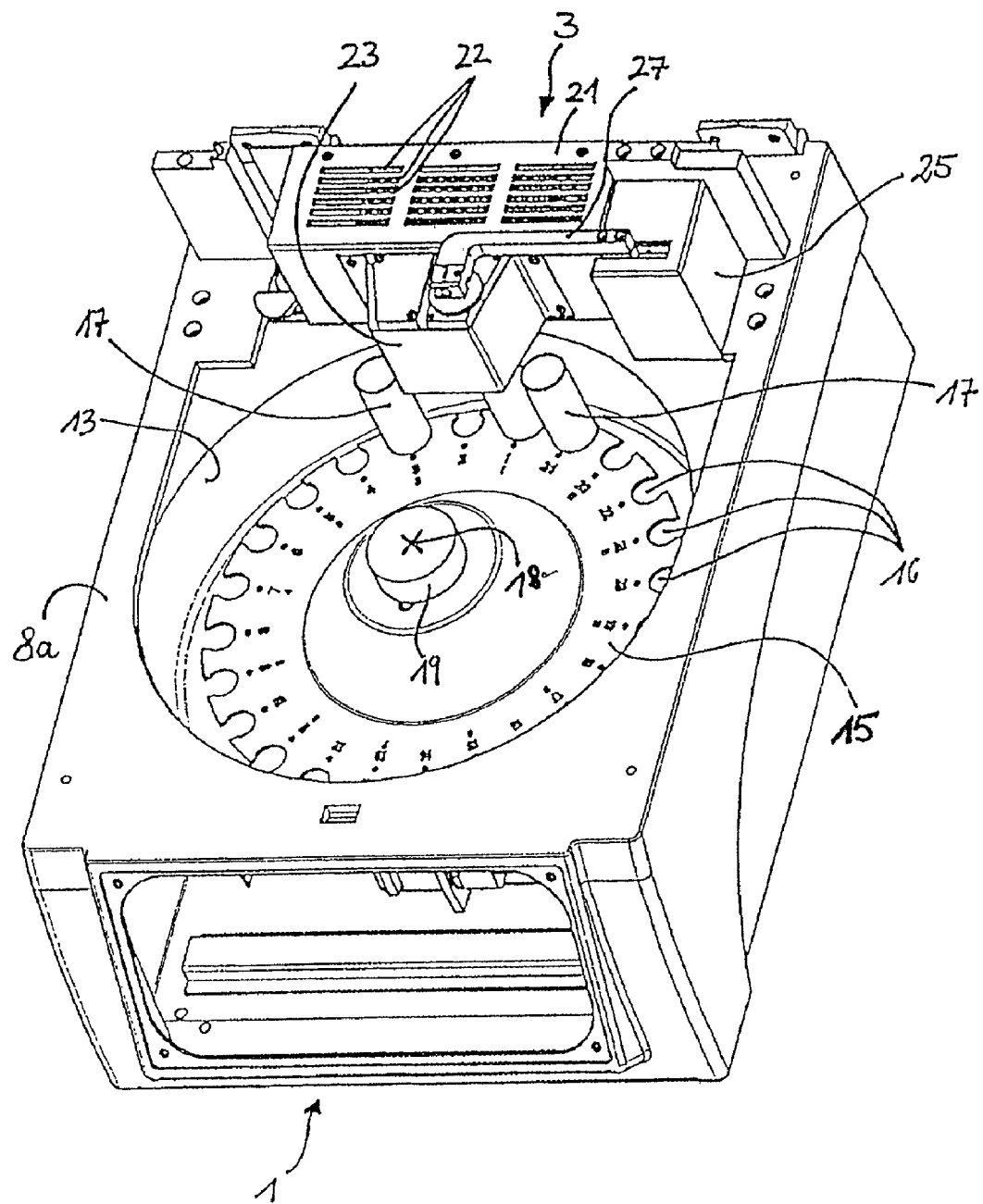
FIG. 4 is a perspective view of the apparatus for tissue preparation for tissue embedding.

FIG. 4 shows a perspective view of an apparatus 1 meant for tissue preparation for the tissue embedding. The cover that is also meant to be there is not shown. The side wall 5 has an inner upper side 8a that is provided with a free space 13. The free space gives access to the inside of apparatus 1. The free space 13 gives access to the transport plate 15 located inside the side wall 5. In this model the transport plate 15 is designed in a round shape and at its edges it has a plurality of recesses 16, which accommodate processing containers 17. In the processing containers 17 the containers for tissue processing for tissue embedding are immersed in the processing liquids. Processing containers 17 of different sizes can be put on transport plate 15 so that even containers of different size can be used. Depending on the microscopic observation method tissue pieces of different sizes have to be prepared.

The transport plate 15 is freely rotable around an axle 18 and in addition it is raisable and lowerable in the direction of the axle 18. The transport plate 15 is secured with the help of securing element 19. The side wall 5 is attached to a heating- and cooling device 3. The heating and cooling device consists of a power supply 21 that is equipped with several vent openings 22 in order to take away the heat. The power supply 21 is attached to an accommodation 23 designed for the processing containers 17. The accommodation is located in such a way that it extends at least partially in the free space 13. As already mentioned above the transport plate 15 is raisable and lowerable in the direction of the axle 18. In a raised position there is at least one processing container 17 in the accommodation 23 and the container can be tempered accordingly. In the processing containers there is a variety of liquids that are necessary for the preparation of the tissue samples. Next to the heating- and cooling device 3 there is a mechanism 25 that is linked to an arm 27. One or several containers containing the individual tissue sample are located onto the arm 27 with the container undergoing the corresponding tissue processing program. The arm 27 is movable up and down so that the container and the tissue samples are immersed in the processing liquid that is in that processing container which is located in accommodation 23 at that very moment.

Figure 5:
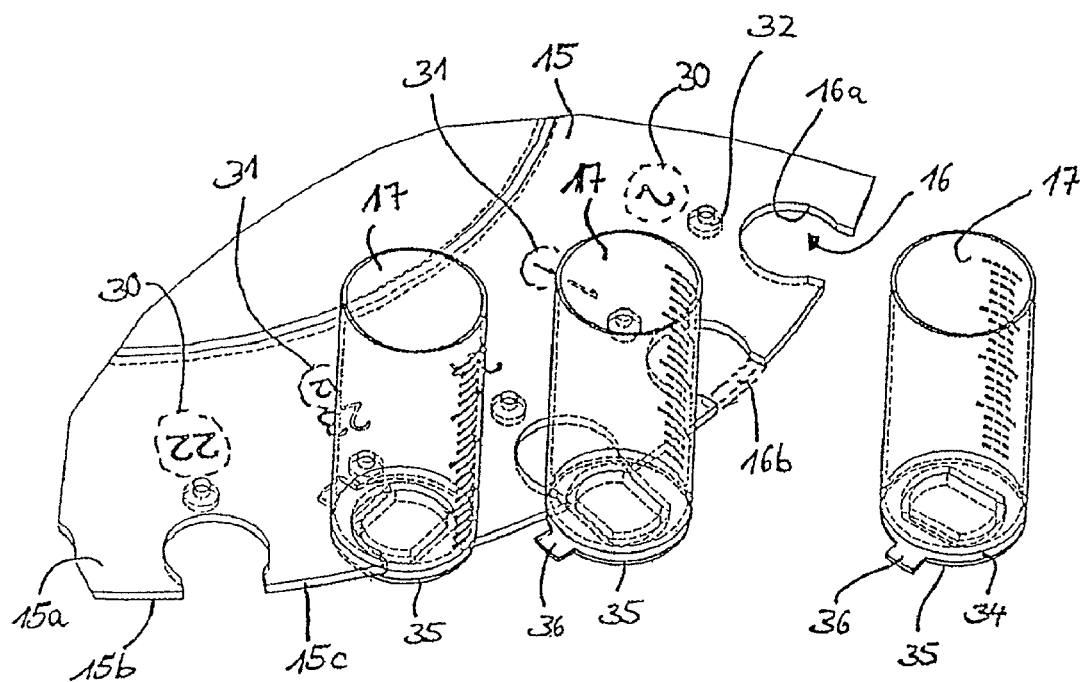
FIG. 5 is a perspective partial view of the transport plate together with the processing containers for tissue preparation.

FIG. 5 gives a partial view of the transport plate 15. FIG. 5 also shows how the processing container 17 acts in combination with the transport plate 15. The transport plate 15 also has an upper side 15a and an under side 15b. A first set of numbers 30 is supposed to be on the upper side 15a of the transport plate 15. The set is located directly opposite to the recesses 16. A second set of numbers 31 is also located on the upper side 15a of the transport plate 15 in such a way that one number matches only every other recess 16. In doing so, the first set of numbers 30 applies to the small processing container 17a (as also shown in FIG. 5) and the second set of numbers 31 applies to the large processing container 17b. Between the first set of numbers 30 and the recess 16 there is a indent 32 in the transport plate 15 that forms a hill on the under side 15b of the transport plate 15. The recess 16 consists of a circular cut out 16a that has an opening 16b at the edge 15c of the transport plate. The opening is smaller than the diameter of the recess 16. The processing containers 17 do preferably have a cylindrical shape and they have a circumferential notch 34 that is the size of the circumferential edge 15c of the transport plate 15. A circular disk 35 at the side opposite to the floor 33 also finishes the circumferential notch 34. The circular disk 35 has a nose 36 that cooperates with the indent 32 at the under side 15b of the transport plate 15.

The invention was described with respect to a specific embodiment of the invention form. It is however obviously that changes and modifications can be carried out without leaving the scope protection of the claims below.

| | |
|---|---|
| 1 | apparatus |
| 2 | container |
| 3 | heating- and cooling device |
| 4 | cylindrical base body |
| 5 | side wall |
| 6 | floor |
| 7 | removable cover |
| 8a | inner upper side |
| 10 | plurality of openings |
| 12 | slit shaped opening |
| 13 | free space |
| 15 | transport plate |
| 15a | upper side |
| 15b | underside |
| 15c | circumferential edge |
| 16 | recess |
| 16a | circular cut out |
| 16b | opening |
| 17 | processing container |
| 18 | axle |
| 19 | securing element |
| 21 | power supply |
| 22 | vent opening |
| 23 | accommodation |
| 25 | mechanic |
| 27 | arm |
| 30 | first set of numbers |
| 31 | second set of numbers |
| 34 | circumferential notch |
| 35 | circular disk |
| 36 | nose |
| 40 | circular opening |
| 42a | groove |
| 42b | elongated groove |
| 43 | bridge in the cover |
| 50 | bridge in the base element |
| 52 | sub-container |
| 53 | hollow cylinder |
| 53a | central opening |
| 54 | circumferential edge |
| 60 | stack |
| 62 | rod |
| 63 | drilling |
| 64 | holding element |
| 66 | securing element |
| 68 | height of the side wall |

We claim:

1. A container for tissue preparation for the tissue embedding, comprises:
    a plurality of base bodies, each of said base bodies having a central hollow cylinder, a cylindrical shaped side wall, a floor and several bridges, whereby the bridges subdivide the containers into several sub-containers and a plurality of slit shaped openings are formed in the cylindrical shaped side wall and extend essentially over the total height of the cylindrical shaped side wall,
    a rod, said rod including a plurality of drillings located along the length of said rod; and,
    a holding element;
    wherein said plurality of base bodies are put together to a stack, whereby the base body on top of the stack is closed with a cover, that the floor of a base body is the cover for a base body arranged downstream on the stack, and that the base bodies are aligned along a groove in the side wall of the base body; and,
    wherein said holding element is inserted through at least one of said plurality of drillings to hold the stack in a fixed position, wherein the rod is lead through the central hollow cylinder and thereby defining an exact position of the base bodies within the stack.

2. The container as defined in claim 1, wherein the bridges are distributed equally on the base body, wherein the bridges end on one side at the side wall of the base body and on the other side at the central hollow cylinder.

3. The container as defined in claim 1, wherein said cover includes a groove, and the groove in the cover and the groove in the base body are in line, if the cover is placed on the base body.

* * * * *